United States Patent [19]

Ventura

[11] Patent Number: 5,572,324
[45] Date of Patent: Nov. 5, 1996

[54] PORTABLE DENT HIGHLIGHTING UNIT

[75] Inventor: George Ventura, Shawnee, Kans.

[73] Assignee: It's Dents Or Us, Inc., Overland Park, Kans.

[21] Appl. No.: 486,113

[22] Filed: Jun. 7, 1995

Related U.S. Application Data

[63] Continuation-in-part of Ser. No. 432,797, May 2, 1995, which is a continuation-in-part of Ser. No. 247,640, May 23, 1994, Pat. No. 5,436,726.

[51] Int. Cl.⁶ .................................................. G01N 21/00
[52] U.S. Cl. ........................................... 356/371; 356/237
[58] Field of Search .................................. 356/237, 371, 356/376

[56] References Cited

U.S. PATENT DOCUMENTS

| | | | |
|---|---|---|---|
| 4,448,527 | 5/1984 | Milana | 356/237 |
| 4,629,319 | 12/1986 | Clarke et al. | 356/237 |
| 4,792,232 | 12/1988 | Jobe et al. | 356/237 |
| 5,090,804 | 2/1992 | Wong et al. | 356/237 |
| 5,168,322 | 12/1992 | Clarke et al. | 356/237 |
| 5,206,700 | 4/1993 | Reynolds et al. | 356/237 |
| 5,225,890 | 7/1993 | Lee et al. | 356/371 |
| 5,237,404 | 8/1993 | Tanka et al. | 356/376 |
| 5,367,378 | 11/1994 | Harding et al. | 356/376 |
| 5,414,518 | 5/1995 | Yazejian | 356/371 |
| 5,436,726 | 7/1995 | Ventura et al. | 356/371 |

FOREIGN PATENT DOCUMENTS

| | | | |
|---|---|---|---|
| 269006 | 11/1988 | Japan . | |
| 213509 | 8/1989 | Japan | 356/371 |
| 264448 | 10/1993 | Japan . | |

OTHER PUBLICATIONS

Hugh W. Lippincott and Henry Stark; Optical–Digital Detection Of Dents And Scratches On Specular Metal Surfaces; Aug. 15, 1982; *Applied Optics*, vol. 21, No. 16, pp. 2875–2881.

Photographs of dent highlighting panel (Attached as Exhibit A to Information Disclosure Statement) (no date).

*Primary Examiner*—Richard A. Rosenberger
*Attorney, Agent, or Firm*—Litman, McMahon and Brown, L.L.C.

[57] ABSTRACT

A portable dent highlighting unit for inspecting a surface of an automobile or other structure for imperfections includes a light box and a power supply unit. The light box comprises a framework having an open front face and a fluorescent lamp secured therein. A lens is removably securable to the framework to extend across the open front face such that the lamp is positioned therebehind. Opposed front and back surfaces of the lens are painted or formed with alternating areas of light and dark colors. On one side, the light areas are yellow, and on the other they are white. The light box is supported on support arms which are magnetically securable to automobile body panels. The power supply unit includes an internal battery, a converter, an electrical connector connectable to an outside power source and a switch. The lamp in the light box is selectively connectible to the internal battery or an outside power source through the converter.

32 Claims, 2 Drawing Sheets

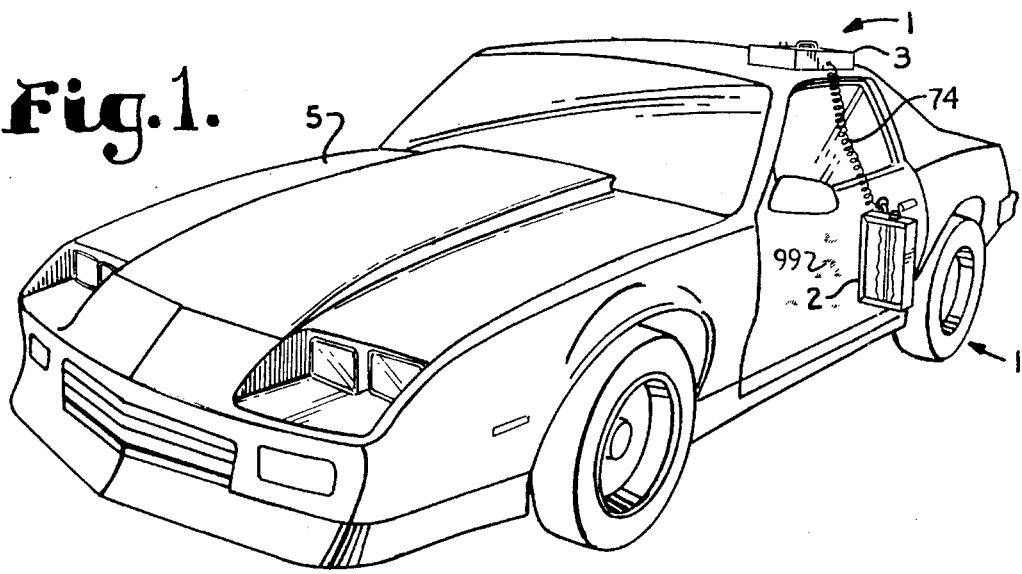
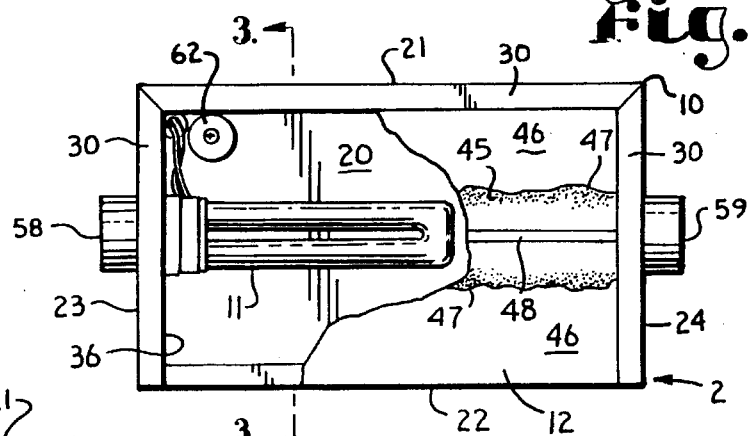
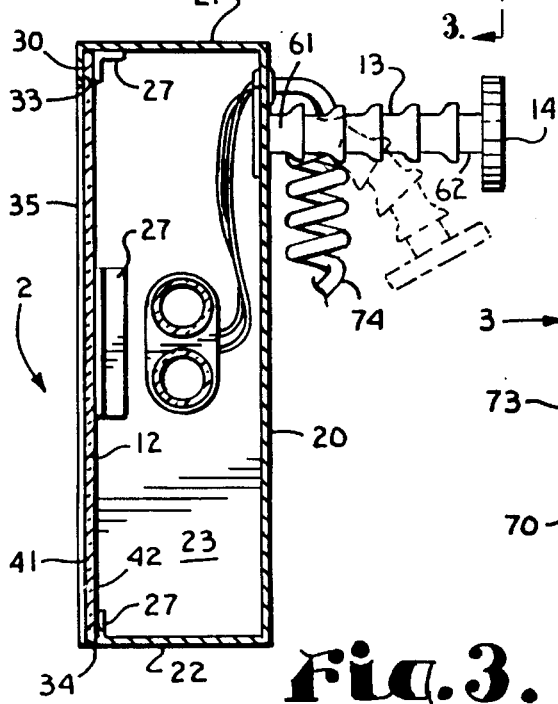
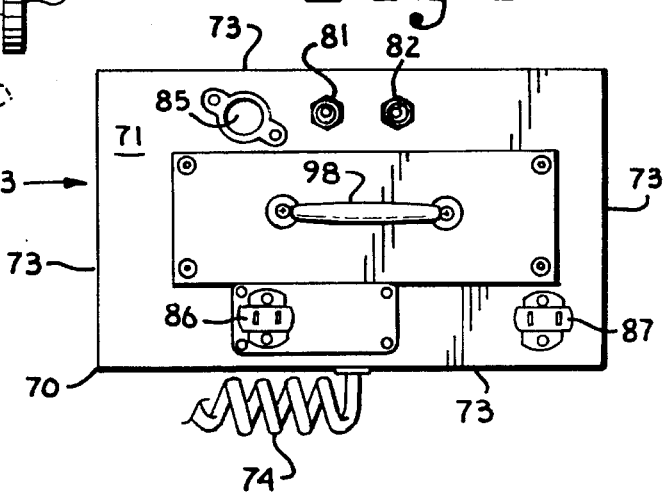

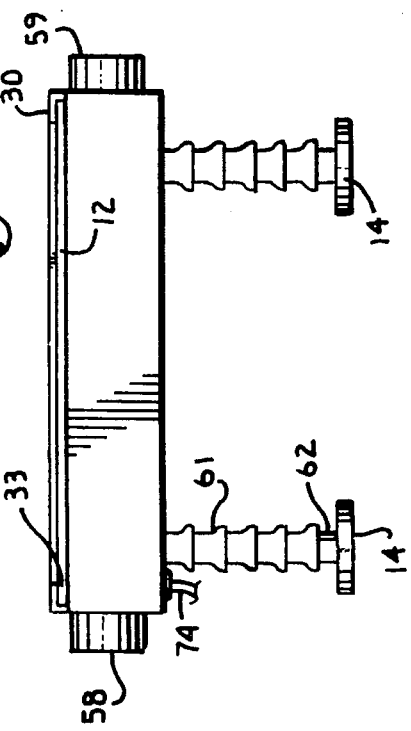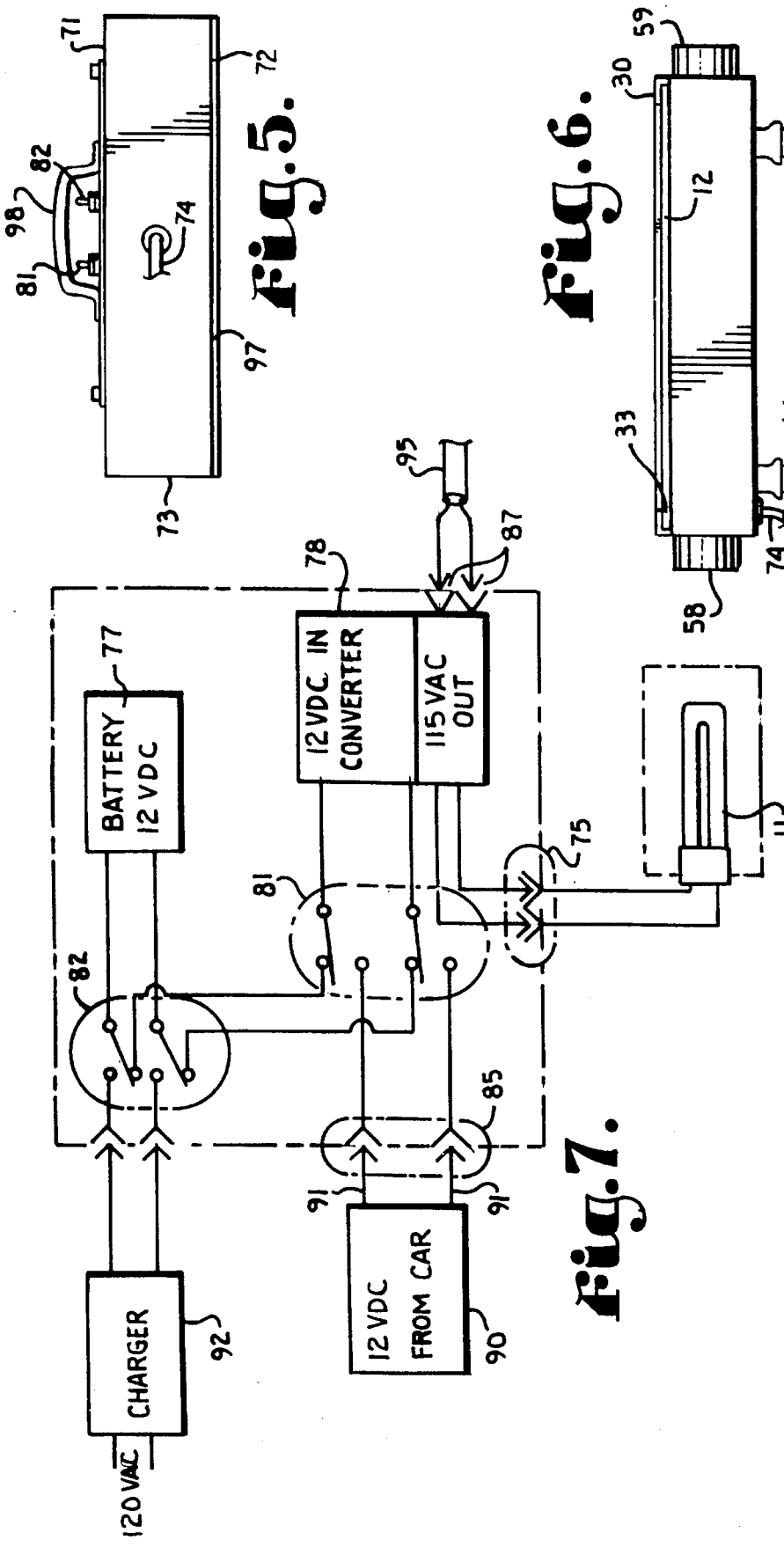

PORTABLE DENT HIGHLIGHTING UNIT

CROSS REFERENCE TO RELATED APPLICATIONS

This application is a continuation-in-part of application Ser. No. 08/432,797, entitled INFINITELY ADJUSTABLE AUTOMOBILE BODY REPAIR LIGHT PANEL SUPPORT, filed May 2, 1995 which is a continuation-in-part of application Ser. No. 08/247,640, entitled FLAW HIGHLIGHTING LIGHT PANEL AND BOOTH FOR AUTOMOBILE BODY REPAIR, filed May 23, 1994, now U.S. Pat. No. 5,436,726.

BACKGROUND OF THE INVENTION

I. Field of the Invention

The present invention relates to an automobile body inspection light panel which is removably securable to a portion of an automobile body for facilitating inspection and repair of automobile bodies.

II. Description of the Related Art

It is often difficult to detect small dents and other imperfections in the surface of an automobile body by unaided eyesight. This is particularly true of new or newly painted automobiles viewed under artificial light, such as in automobile assembly plants or repair and paint shops. In such assembly plants and repair shops, it is important that even the smallest dent or imperfection be detected to provide for satisfied customers and dealers and to avoid adversely affecting the reputation of the plant or shop.

Several previous efforts have been made to produce inspection systems for metal surfaces which are designed to detect surface dents and scratches. Hugh Lippincott and Henry Stark, in an article entitled "Optical-digital detection of dents and scratches on specular metal surfaces" in Applied Optics, Aug. 15, 1982, describe a system in which a regular grid pattern is reflected off of a metal surface to be inspected, with the reflected image photographed by a video camera. The photographs are then digitally analyzed and compared against samples from a calibration sample from an unflawed surface with any large deviations indicating the presence of one or more dents. For scratch detection, the authors describe a gray level threshold analysis to detect background to scratch brightness contrasts. The system described in the Applied Optics article was designed for and appears to be most suitable for implementation in an environment in which relatively small manufactured appliances must be inspected automatically, with badly scratched or dented samples simply discarded or recycled.

A series of U.S. Patents describe a retroreflective surface inspection system and method, including Pat. No. 4,629,319 to Clarke et al., Pat. No. 5,168,322 to Clarke et al., and Pat. No. 5,206,700 to Reynolds et al., all of which are assigned to Diffracto, Ltd. of Windsor, Canada. In these patents, light from a slit or point source is swept across a surface to be inspected via a scanning mirror or the like. The light reflects off of the inspected surface, off of a retroreflective surface and back off of the inspected surface and then to a camera lens or the eye of an observer. The retroreflected image received by the camera or eye magnifies any dents or imperfections in the surface being inspected. These systems employ sophisticated robotic inspectors and require complex synchronization of the swept beam and the analyzing equipment. For use in an automobile assembly plant or the like, the patents illustrate an inspection system with multiple independent light emitters, reflectors and analyzers. In addition, these patents describe an inspection process in which inspected panels must first be covered with a thin coating of oil to enhance their reflective properties. This is an expensive and time consuming process. Finally, in the Diffracto systems, as well as the Lippincott and Stark article, a sophisticated digital analysis must be performed and interpreted, which effectively limits the possibility of immediate correction of detected dents or other defects.

It is clear then, that an effective apparatus and method is needed for highlighting flaws and imperfections in automobile bodies. Such an apparatus and method should be inexpensive and reliable, should allow flaws and imperfections to be detected quickly and efficiently by an ordinary observer, should be effective at highlighting flaws in automobiles of a wide variety of colors and should allow detected dents and blemishes to be repaired immediately during the inspection process. Such a highlighting apparatus should be capable of convenient transport to an automobile to be inspected, and should be positionable to highlight almost any surface of an automobile to be inspected or repaired. Further such an apparatus should be operable to highlight dents regardless of the ambient light conditions.

SUMMARY OF THE INVENTION

The present invention is directed to a portable automobile body inspection light panel to facilitate inspection of an automobile body surface for flaws or imperfections.

The portable light panel includes a light source secured within a framework or housing. A lens is securable to the framework such that the light source is positioned behind the lens and the light source directs light through the lens. One side of the lens is colored translucent white and has an opaque black stripe painted or otherwise applied thereon. A narrow centerline extending through the opaque black stripe may be left white. The opposite side of the lens is colored translucent yellow with an opaque black stripe painted thereon. A narrow centerline extending through the opaque black stripe may similarly be left as yellow. The lens is securable to the framework such that the opposite sides of the lens are selectively directed away from the light source depending on the color of light to be cast onto the surface.

The portable light panel is removably securable to an automobile by means such as magnets connected to a pair of flexible arms. Each arm is secured at one end to one of the magnets and at a second end to the framework. The magnets may be magnetically coupled to an automobile body panel such that the framework and lens are spaced slightly away from the surface to be inspected. The flexible arms may be adjusted to adjust the relative orientation of the lens to the surface to be inspected such that light from the light source and lens are cast in the appropriate spot for inspection of the surface.

Depending upon the color of the automobile being inspected, one or the other side of the lens is directed toward the automobile to project a light pattern onto the automobile body surface.

The projected light pattern highlights the visibility of any flaws or imperfections in the body surface by magnifying an observer's perception of relative depth differences between the flaw and the unflawed body surface. The white lens side is used for automobiles with darker shades of color, such as black, navy blue, maroon, etc. while the yellow lens side is more effective at highlighting and enhancing imperfections in lighter colored automobiles, such as white, light gray, light blue, etc.

The black stripes are painted or otherwise applied to the yellow and white lenses in a fashion such that the black color irregularly "bleeds" into the yellow or white. This technique forms shadow areas between translucent yellow and opaque black, which shadow areas are projected onto the automobile by the backlights. The thus created shadow lines form light patterns on the automobile body which highlight any dents or imperfections in the automobile body surface by making the dents appear darker than the surrounding smooth surface, which appears to shine by contrast. The narrow centerlines are positioned to serve as a reference in aligning the light panel, i.e. the centerline projects a narrow strip of light within a dark band so that the dark band can be centered on a dent to be repaired.

The portable light panel is electrically connectable to a power source such as a standard electrical outlet, the electrical system of the automobile being inspected or a separate battery. Providing a separate battery or connection into the electrical system of a car to be inspected permits use of the portable light panel at remote locations where a standard outlet may not be accessible, such as on an automobile sales or car rental lot. Further, such an arrangement permits use of the light panel in situations where it would be impractical and potentially dangerous to use a lengthy extension cord to provide power to the light source. For example, use of the portable light panel with a separate battery pack or means to connect into an automobile electrical system is particularly well adapted for use on an auto assembly line where the light panel can be attached to a car as it is proceeding down the assembly line so dents can be repaired without interrupting the assembly process.

OBJECTS AND ADVANTAGES OF THE INVENTION

The objects and advantages of the present invention include: providing a portable light panel which highlights flaws and imperfections in an automobile body surface; providing such a light panel which includes a specially colored lens or lenses which, when backlighted, project light patterns and shadow lines onto the automobile body which patterns highlight any imperfections in the surface; providing such a light panel which has a translucent white and opaque black striped lens for highlighting surface flaws in darker colors and a translucent yellow and opaque black striped lens for highlighting surface flaws in lighter colors; providing such a portable light panel in which each opaque black stripe includes a narrow centerline of translucent white or yellow to serve as a centerline reference; providing a light panel support which is easily transportable; providing such a light panel which can be releasably secured to an automobile to be inspected; providing such a light panel which permits adjustment of the orientation of the lens with respect to the surface to be inspected; providing such a light panel for which power may be supplied from a standard outlet, a portable power source such as a battery or from the electrical system of an automobile to which the light panel is secured; and providing such a light panel which is reliable, inexpensive and relatively simple to manufacture and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a portable dent highlighting unit of the present invention comprising a light box and a power supply unit secured to and positioned on an automobile for inspection of a surface of the automobile.

FIG. 2 is an enlarged front elevational view of the light box of the present invention with portions broken away to show interior detail.

FIG. 3 is an enlarged and fragmentary cross-sectional view of the light box taken along line 3—3 of FIG. 2 showing adjustability of a support arm for the light box in phantom lines.

FIG. 4 is an enlarged and fragmentary top plan view of the power unit.

FIG. 5 is an enlarged elevational view of the power unit of the present invention.

FIG. 6 is an enlarged side elevational view of the light box of the present invention.

FIG. 7 is a schematic diagram of the power unit providing power to the light box.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in greater detail, the reference numeral 1 refers to a portable dent highlighting unit of the present invention. The portable dent highlighting unit 1 includes a light box 2 and a power supply unit 3. FIG. 1 shows the light box 2 affixed to the door of an automobile 5 and the power supply unit 3 positioned on the roof of the automobile 5.

The light box 2 is shown in greater detail in FIGS. 2, 3 and 6. The light box 2 comprises a framework 10, a light source 11, a lens 12, a pair of support arms 13 and magnets 14. The framework 10 generally comprises a rectangular box with an open face. The framework includes a back panel 20, side panels 21 and 22, end panels 23 and 24, internal shoulder or lip 27 and external shoulder or lip 30. The internal shoulder 27 extends at least partially along and inward from an upper end of the side panels 21 and 22 and the end panels 23 and 24. The external shoulder 30 is spaced above the internal shoulder 27 and extends at least partially along and inward from the upper end of the end panels 23 and 24 and the side panel 21. The internal and external shoulders 27 and 30 define a lens receiving slot 33 extending therebetween with a slot opening 34 extending along the length of side panel 22.

A first side or front face 35 of the framework 10 is generally left open except for the internal and external shoulders 27 and 30 which extend partially across the front face 35 and define a light box opening 36. The lens 12 is of rectangular dimensions and may be slid into and secured within the slot 33 such that the lens 12 extends across the light box opening 36 and the front face 35 of the framework 10.

The lens 12 includes a first lens surface 41 and an opposed second lens surface 42. Each lens surface 41 and 42 is of a translucent, light color with a centered, opaque, dark colored stripe 45, which leaves outside bands 46 of the original light color. The light colored bands 46 on the first lens surface 41 are preferably translucent yellow while the bands 46 on the second lens surface 42 are preferably translucent white. The yellow lens surface 41 is more effective for inspection of lighter colored automobiles, such as white, light gray, silver, etc. while the white lens surface 42 is more effective for darker colored automobiles, such as dark gray, black, brown, etc. The dark stripes 45 tend to bleed into the light bands 46, creating a wavy and indistinct shadow line 47 therebetween. A narrow centerline 48 of the original light color of each lens surface is left for a reference in centering a dent to be repaired in the dark stripe 45.

The lens 12 is reversible in that it may be secured within the slot 33 such that either the first lens surface 41 or the second lens surface 42 is directed away from the light box 2 and the light source 11.

The light source 11 preferably comprises a fluorescent lamp mounted within the framework 10. As generally shown in FIG. 2, the lamp 11 is fixedly mounted to end wall 23 and is generally spaced behind lens 12. Handles 58 and 59 are fixedly secured to and project outward from end panels 23 and 24 respectively.

The support arms or structural members 13 are each secured at a first end 61 to the back panel 20 of the framework 10. One of the magnets 14 is secured to a second end 62 of each support arm 13 and spaced away from the framework 10. The support arms 13 are preferably constructed of materials or in a manner such that the arms 13 are sufficiently flexible to permit bending of the arms 13 upon application of a slight manual force while being sufficiently rigid to retain the relative alignment or shape of the arms after bending and under the weight of the framework 10, lamp 11 and lens 12. The arms 13 with magnets 14 secured to one end thereof as shown in FIG. 3 are constructed of products distributed by Lockwood Products, Inc., 5615 SW Willow Lane, Lake Oswego, Oreg., 97035 under the trademark LOC-LINE and having part numbers of 60531 and 60532 respectively.

The light box 2 may be removably securable to an automobile 5, by affixing the magnets 14 to an automobile body panel adjacent an area on the automobile 5 to be inspected. The relative orientation of the front face 35 and the lens 12 of the light box 2 with respect to the area to be inspected may be adjusted by applying a force on the framework 10 or arms 13 to bend the arms 13 to result in the desired orientation of the lens 12. The handles 58 and 59 are provided to facilitate adjusting the orientation of the light box 2.

Referring to FIGS. 4, 5 and 7, the power supply unit 3 comprises a housing 70 having an upper surface 71, a lower surface 72 and side walls 73. Secured within the housing 70, as shown schematically in FIG. 7, is a 12 volt battery, which for the purposes of this application will be referred to as the internal battery 77, and an AC/DC converter 78. The power supply unit 3 is electrically connected to the light box 2 through flexible cord 74. The cord 74 is connected at one end to a first electrical connector 75 mounted on one of the side walls 73 of the power supply unit 3. The first electrical connector 75 is also connected to the converter 78. The other end of the cord 74 is connected to the light source 11.

A first switch 81 and a second switch 82 are mounted on the upper surface 71 of the power supply unit 3. A second electrical connector 85, a third electrical connector 86 and a fourth electrical connector 87 are secured in the upper surface 71 of the housing 70.

The converter 78 is of the type adapted to convert direct current from a 12 volt battery to alternating current of ordinary household line voltage, i.e. approximately 110 to 120 volts. The converter 78 is selectively connected to the internal battery 77 or the second connector 85 via switch 81. The second connector 85 may be connected to an external battery 90, such as a car battery, via a cord 91. The cord 91 is connected at one end to the second electrical connector 85 and at a second end to the external battery 90 in the automobile 5. Although not shown the cord 91 is preferably adapted for connection to the car battery 90 through the car cigarette lighter (not shown).

The internal battery 77 is selectively connected to the converter 78 or the third electrical connector 86 via the second switch 82. A charger 92 is connectable to the third connector 86. Thus, when the internal battery 77 is to be used to supply power to the light source 11, it must be connected to the converter 78 through both the first and second switches 81 and 82.

The fourth electrical connector 87 is connected to cord 74 via the converter 78. Therefore, power may also be supplied to the light source 11 from a standard 120 volt outlet (not shown) by running an extension cord 95 from the outlet and connecting it to the fourth electrical connector 87. A third switch (not shown), can be used to permit connection of the extension cord 95 to the cord 74 via the converter 78.

A magnet 97, preferably a sheet type magnet, is secured to the lower surface 72 of the power supply unit housing 70. The housing 70 may be magnetically secured to body panels of the automobile 5 formed of magnetically attractable metals. The magnetic connectability of the housing 70, permits securement of the power supply unit 3 to the hood, trunk or roof of most automobiles. The power supply unit 3 also includes a handle 98 secured to the upper surface 71 thereof. The handle 98 facilitates carrying of the power supply unit 3.

The power supply unit 3 permits use of the light box 2 at almost any location whether or not a separate power source is available. Further, the ability to removably secure the light box 2 to most automobile body panels permits placement of the light box 2 adjacent to almost any metal surface on an automobile 5 on which repairable dents and imperfections, such as dent 99, may occur. Such flexibility in placing the light box 2 where desired, permits reliable detection of the dents 99 on any portion of the automobile body.

A workman who is to remove dents and imperfections from a portion of an automobile body, such as a door, for example, will position the light box 2 such that it shines an optical shadow line pattern onto the door, with the projected centerline 48 centered in the dent 99 to be repaired. The workman observes the light pattern reflected by the door continuously while he straightens the dent 99. With the inventive dent highlighting unit, the workman can constantly highlight the door as he straightens the dent 99, thus making him immediately aware of when the dent 99 is straightened, or when further straightening is needed.

The portable dent highlighting unit 1, is ideal for use to detect and repair dents 99 on automobiles 5 as they are advanced along an assembly line because the power supply unit 3, incorporating its own power source in the internal battery 77 permits use of the light box 2 without the need for connection to a fixed power source. The light box 2 and power supply unit 3 can be secured to a car as it travels down the assembly line and the workman can repair any dents 99 without stopping the assembly line or taking the car off the line. The unit 1 is also ideal for use on automobiles located in outdoor sales lots, parking lots, parking garages or indoor garages or showrooms when lighting is poor and access to fixed power sources is limited.

It is contemplated that other means, other than magnets 14 could be used to removably secure the light box 2 to an automobile. For example, the magnets could be replaced by suction cups which would permit attachment of the light box to a wider range of materials and surfaces including windows, plastic bumpers and nonmetallic body panels as well as metallic body panels. In addition, structure could be provided for mechanically connecting the light box 2 to different portions of an automobile such as through the use of clamps and the like.

It is also foreseen that the support arms 13 would not be necessary and the magnets 14 or other securement means could be mounted directly to the framework 10 of the light box 2. Means other than the support arms 13 described above could be used to secure the framework 10 to the magnets 14 to space the framework 10 and lens 12 away from the surface. Such means could include use of rigid arms or support members and a rotatable connection between the framework and the rigid arms.

It is also foreseen that the lens 12 may be secured to the light box 2 by means other than insertion in slot 33, including use of clamps and adhesives. Further it is foreseen that the light box 2 could be designed such that separate lenses, a white lens and a yellow lens, could be secured to the framework 10 on opposite sides of the light source 11 thereby eliminating the need to reverse the lens to use the different colored lens surface. Further, although the patterns on the lens surfaces 41 and 42 are described as alternating light colored bands and opaque dark colored stripes, the pattern could be any configuration of at least one translucent light colored area adjacent to at least one opaque dark colored area such that the pattern presents a transition zone or line from the light colored area to the dark colored area.

In the preferred embodiment, the power supply unit 3 is structurally separated from the light box 2 because the weight and size of the battery 17 and converter 78 make it impractical to incorporate these items into a single housing or framework with the light source and lens. The added weight and size of such a light box would make the light box unwieldy and difficult to secure to an automobile body panel with reasonably priced and sized magnets. However, it is foreseen that the power supply unit 3 could be structurally incorporated into the light box 2. If the size and weight of available batteries and converters are reduced sufficiently, it may become practical to structurally incorporate these items into the light box. Although use of fluorescent lighting as the light source 11 is preferred, the unit could be adapted to use DC powered halogen lights or the like powered directly from the battery without the need for a converter 78. Elimination of the need for the converter 78 might make incorporation of the power supply unit 3 into the light box 2 practical. Further use of stronger magnets 14 may make incorporation of the power supply unit 3 into the light box 2 practical.

Although the preferred embodiment was disclosed as incorporating a magnet 97 on the power supply unit 3, use of the magnet or any other means for releasably securing the power supply unit 3 to an automobile body panel is optional. In use, the power supply unit could simply be set on one of the seats of the automobile 5 during use or on the hood of the automobile 5 without means for securing the unit 3 thereto.

It is to be understood, that although use of the portable dent highlighting unit 1 has been described with respect to its use to detect dents on automobiles, the unit 1 could be used to detect dents on the surface of almost any structure, particularly structures incorporating metal surfaces.

It is to be understood that while certain forms of the present invention have been illustrated and described herein, it is not to be limited to the specific forms or arrangement of parts described and shown.

What is claimed and desired to be secured by Letters Patent is as follows:

1. A portable highlighting unit for inspecting a surface of a structure for imperfections comprising:
   a. a framework having a first side;
   b. a light source supported by said framework and spaced behind said first side;
   c. a lens securable to said first side of said framework to cover at least a portion of said first side of said framework; said lens including a first lens surface having at least one translucent light colored area adjacent to at least one opaque dark colored area; and
   d. mounting means secured to said framework for releasably securing said framework to the structure such that said first lens surface may be positioned to face the surface to be inspected.

2. A portable highlighting unit as in claim 1 wherein:
   a. said lens includes a second lens surface on an opposite side of said lens from said first lens surface; said second lens surface having at least one translucent light colored area adjacent to at least one opaque dark colored area, said translucent light colored area(s) on said second lens surface being of a different color than those on said first lens surface; and
   b. said portable dent highlighting unit includes means for removably securing said lens to said framework such that said first lens surface and said second lens surface may be selectively and alternatively directed away from said light source and toward the surface to be inspected.

3. A portable highlighting unit as in claim 2 wherein:
   a. each of said dark areas on said first and second lens surfaces is applied to the respective lens surface such that the dark color bleeds into the translucent light colored areas to form shadow lines.

4. A portable highlighting unit as in claim 2 wherein:
   a. each of said opaque dark colored areas includes a narrow centerline of said translucent light color.

5. A portable highlighting unit as in claim 2 wherein:
   a. said first lens surface includes alternating yellow and black areas.

6. A portable highlighting unit as in claim 5 wherein:
   a. said first lens surface of alternating yellow and black areas is effective for highlighting defects in lighter colored surfaces.

7. A portable highlighting unit as in claim 2 wherein:
   a. said second lens surface includes alternating white and black areas.

8. A portable highlighting unit as in claim 7 wherein:
   a. said second lens surface of alternating white and black areas is effective for highlighting defects in darker colored automobile bodies.

9. A portable highlighting unit as in claim 1 wherein:
   a. said light source comprises a fluorescent lamp.

10. A portable highlighting unit for inspecting a surface of a structure for imperfections comprising:
    a. a framework having a first side;
    b. a light source supported by said framework, spaced behind said first side of said framework and connectable to a power source;

c. a lens securable to said first side of said framework to cover at least a portion of said first side of said framework; said lens including a first lens surface having at least one translucent light colored area adjacent to at least one opaque dark colored area, and d. at least one structural member connected at a first end to said framework and connected at a second end to mounting means for releasably securing said structural member to the structure; said structural member spacing said framework away from the structure and including adjustment means for adjusting the orientation of said framework and said first lens surface with respect to the surface to be inspected.

11. A portable highlighting unit as in claim 10 wherein said structural member comprises a flexible arm.

12. A portable highlighting unit as in claim 10 wherein said mounting means comprises a magnet.

13. A portable highlighting unit as in claim 10 further comprising a portable power source electrically connectable to said light source.

14. A portable highlighting unit as in claim 10 wherein:

a. said lens includes a second lens surface on an opposite side of said lens from said first lens surface; said second lens surface having at least one translucent light colored area adjacent to at least one opaque dark colored stripes, said translucent light colored area(s) on said second lens surface being of a different color than those on said first lens surface; and b. said portable dent highlighting unit includes means for removably securing said lens to said framework such that said first lens surface and said second lens surface may be selectively and alternatively directed away from said light source and toward the surface to be inspected.

15. A portable highlighting unit as in claim 14 wherein:

a. each of said dark areas on said first and second lens surfaces is applied to the respective lens surface such that the dark color bleeds into the translucent light colored areas to form shadow lines.

16. A portable highlighting unit as in claim 14 wherein:

a. each of said opaque dark colored areas includes a narrow centerline of said translucent light color.

17. A portable highlighting unit as in claim 14 wherein:

a. said first lens surface includes alternating yellow and black areas.

18. A portable highlighting unit as in claim 17 wherein:

a. said alternating yellow and black areas on said first lens surface are effective for highlighting defects in lighter colored surfaces.

19. A portable highlighting unit as in claim 14 wherein:

a. said second lens surface includes alternating white and black areas.

20. A portable highlighting unit as in claim 19 wherein:

a. said alternating white and black areas on said second lens surface are effective for highlighting defects in darker colored automobile bodies.

21. A portable highlighting unit for inspecting a surface of a structure for imperfections comprising:

a. a framework having a first side;

b. a light source supported by said framework and spaced behind said first side of said framework;

c. a lens securable to said first side of said framework to cover at least a portion of said first side of said framework; said lens including a first lens surface having at least one light colored area adjacent to at least one opaque dark colored area; and d. at least one structural member connected at a first end to said framework and connected at a second end to mounting means for releasably securing said structural member to the stucture; said structural member spacing said framework away from the structure and including adjustment means for adjusting the orientation of said framework and said first lens surface with respect to the surface to be inspected; and e. a power supply unit electrically connected to said framework to selectively provide power to said light source, said power supply unit including:

i. a battery;

ii. an electrical connector selectively connectable to an external power source; and iii. a switch for selectively connecting said light source to said battery or said electrical connector.

22. A portable highlighting unit as in claim 21 wherein:

a. said power supply unit includes a housing separate from said framework;

b. said battery is secured within said housing; and c. said battery or said electrical connector are selectively connected to said light source by a flexible cord extending between said housing and said framework.

23. A portable highlighting unit as in claim 21 further comprising means for releasably securing said power supply unit housing to the structure.

24. A portable highlighting unit as in claim 21 wherein said structural member comprises a flexible arm.

25. A portable highlighting unit as in claim 21 wherein said mounting means comprises a magnet.

26. A portable highlighting unit as in claim 21 wherein:

a. said lens includes a second lens surface on an side of said lens from said first lens surface; said second lens surface having at least one translucent light colored area adjacent to at least one opaque dark colored area, said translucent light colored area(s) on said second lens surface being of a different color than those on said first lens surface; and b. said portable dent highlighting unit includes means for removably securing said lens to said framework such that said first lens surface and said second lens surface may be selectively and alternatively directed away from said light source and toward the surface to be inspected.

27. A portable highlighting unit as in claim 26 wherein:

a. each of said dark areas on said first and second lens surfaces is applied to the respective lens surface such that the dark color bleeds into the translucent light colored areas to form shadow lines.

28. A portable highlighting unit as in claim 26 wherein:

a. each of said opaque dark colored areas includes a narrow centerline of said translucent light color.

29. A portable highlighting unit as in claim 26 wherein:

a. said first lens surface includes alternating yellow and black areas.

30. A portable highlighting unit as in claim 29 wherein:

a. said alternating yellow and black areas on said first lens surface are effective for highlighting defects in lighter colored surfaces.

31. A portable highlighting unit as in claim 26 wherein:

a. said second lens surface includes alternating white and black areas.

32. A portable highlighting unit as in claim 31 wherein:

a. said alternating white and black areas on said second lens surface are effective for highlighting defects in darker colored automobile bodies.

* * * * *